United States Patent [19]

Regan

[11] 3,976,788

[45] Aug. 24, 1976

[54] ANTIPSYCHOTIC AGENTS

[75] Inventor: Bernard M. Regan, Chicago, Ill.

[73] Assignee: Baxter Laboratories, Inc., Deerfield, Ill.

[76] Inventor: Bernard M. Regan, 5213 N. Ludlam Ave., Chicago, Ill. 60630

[22] Filed: Aug. 5, 1974

[21] Appl. No.: 494,584

Related U.S. Application Data

[62] Division of Ser. No. 373,547, June 25, 1973, abandoned.

[52] U.S. Cl. ............................ 424/342; 260/614 F
[51] Int. Cl.² .......................................... A61K 31/08
[58] Field of Search ..................................... 424/342

[56] References Cited

UNITED STATES PATENTS

| 3,683,092 | 8/1972 | Regan et al. | 424/342 |
| 3,689,459 | 9/1972 | Regan | 424/342 |

*Primary Examiner*—Jerome D. Goldberg

[57] ABSTRACT

Fluoromethyl fluoropropyl ethers, e.g. $CHF_2$—O—$CH_2CF_2CF_3$ and $CHF_2$—O—$CF_2CHFCF_3$, useful for antipsychotic treatment by inhalation sufficient to induce therapeutic convulsions.

1 Claim, No Drawings

ANTIPSYCHOTIC AGENTS

This is a division of Ser. No. 373,547 filed June 25, 1973, now abandoned.

This invention relates to certain fluoromethyl fluoropropyl ethers which are useful as convulsant agents. These agents may be administered by inhalation to provide an alternative to electroconvulsive therapy for a severe depression in a patient who presents an immediate risk of suicide, or a depression that has proved refractory to treatment with an antidepressant drug. Convulsive therapy with these agents also is useful in schizoaffective reactions, especially those with attendant depression, and in acute schizophrenic reactions with excitement or with catatonic withdrawal. The depth and duration of convulsions produced by an inhalant agent is comparatively easy to control, the outset of convulsions is more gradual, the clonic phase tends to last longer, and usually patients express a preference for inhaloconvulsive to electroconvulsive therapy. Consequently, the convulsant agents of this invention provide a practical advantage to antipsychotic therapy.

The convulsant agents of this invention are methyl propyl ethers containing 6–8 fluorine substituents with 1 to 2 fluorines on the methyl moiety and 4 to 6 fluorines on the propyl moiety. They can be described by the following structural formulas:

$CHF_2—O—CH_2CF_2CHF_2$ (I)[4], $CHF_2—O—CH_2CF_2CF_3$ (II), $CHF_2—O—CF_2CHFCF_3$ (III), $CHF_2—O—CF(CHF_2)_2$ (IV)[2], and $CH_2F—O—CH_2CF_2CF_3$ (V)[1]

[1]All footnotes are below Tables 1 to 3.

The preferred convulsant agents of this invention are the ethers I, II, III and IV, which are more stable than V to heat.

The convulsant agents I-V of this invention have each been found to be at least 6 times less lethal than either the closely related known convulsant[3], $CF_3—O—CH_2CF_2CHF_2$(VI) or the well known useful convulsant fluorothyl[5], $CF_3CH_2—O—CH_2CF_3$(VII) in mice (See Table 1).

Another advantage of the convulsant agents of this invention is that the vapor concentrations at which they are convulsant are comparatively easy to control and administer using conventional "anesthetic machines".

It is most surprising that the ethers I-V are convulsant agents, since nine closely related fluoromethyl fluoropropyl ethers containing 6 to 8 fluorine substituents were tested and found to be nonconvulsant in mice; 4 of these were tested and also found to be nonconvulsant in dogs. (See Table 2)

It is further surprising that the ethers I-V are convulsant agents, snce seven related methyl fluoropropyl ethers containing 4 to 7 fluorine substituents were found to be nonconvulsant in mice, and one of these has even been shown to be antagonistic to flurothyl induced convulsions[5]. (See Table 3)

The fluorinated ethers in Tables 1, 2 and 3 were tested by exposing male CF-1 mice to a minimum of three graded concentrations of the test compound admixed with air for 5 minutes in a manner similar to that reported by Robbins.[14] Thirty mice in groups of five in a covered 6.3 liter animal jar were observed for convulsions, anesthesias and other effects. If anesthesia occurred, the median anesthetic concentration ($AC_{50}$) was established. Another thirty mice were treated similarly to establish the median lethal concentration ($LC_{50}$). The concentrations were calculated from the volume used and density of the test compound and the volume of air (6.3 l) in the test jar using the ideal gas law. The results for the convulsant ethers are given in Table 1; Tables 2 and 3 contain the results for related nonconvulsant ethers, most of which are good anesthetic agents.

The convulsant agents I-V are colorless, volatile liquids boiling between 46° C and 76° C with not unpleasant odors and are nonflammable in air.

The ethers I and II can be prepared from 2,2,3,3-tetrafluoropropanol and 2,2,3,3,3-pentafluoropropanol, respectively, and chlorodifluoromethane with sodium or potassium hydroxide, e.g., in the manner described in U.S. Pat. No. 3,689,459. (See Examples 1 and 2)

The ether III can be prepared from methyl 1,1,2,3,3,3-hexafluoropropyl ether and two equivalents of chlorine at 15°–25° C with ultraviolet irradiation to give the dichloromethyl 1,1,2,3,3,3-hexafluoropropyl ether (XXIV), $CHCl_2—O—CF_2CHFCF_3$ XXIV which can be treated with about a 0.67 molar equivalent of bromine trifluoride at 0°–25° C to give the ether III. (See Examples 3 and 4)

The ether IV can be prepared from 1,3-dichloro-1,1,2,3,3-pentafluoro-2-propyl methyl ether and two molar equivalents of chlorine at 15°–25° C with ultraviolet irradiation to give the dichloromethyl 1,3-dichloro-1,1,2,3,3-pentafluoro-2-propyl ether (XXV), $CHCl_2—O—CF(CF_2Cl)_2$ XXV which can be treated with about one molar equivalent of antimony trifluoride and about 0.02 molar equivalent of antimony pentachloride at 60°–90° C to give the 1,3-dichloro-1,1,2,3,3-pentafluoro-2propyl difluoromethyl ether XXVI, $CHF_2—O—CF(CF_2Cl)_2$ XXVI which can, in turn, be treated at about 25° C with a 0.55 molar equivalent of lithium aluminum hydride as a 0.9 molar solution in diethylene glycol diethyl ether to give the ether IV. (See Examples 5, 6 and 7)

The ether V can be prepared by a method analogous to that described by Weinmayr[1], or from methyl 2,2,3,3,3-pentafluoropropyl ether and one molar equivalent of sulfuryl chloride at 0°–35° C with ultraviolet irradiation to give the chloromethyl 2,2,3,3,3-pentafluoropropyl ether XXVII, $CH_2Cl—O—CH_2CF_2CF_3$ XXVII which can be treated with about a 0.4 molar equivalent of bromine trifluoride at −5° C to give the ether V (See Examples 8 and 9). It was found that the ether V was unstable to heat and decomposed with the formation of hydrogen fluoride upon distillation at 760 torr; however, it was stable to 70° C in the presence of an alkaline material, e.g., soda lime.

Although specific methods of preparing the convulsant agents of this invention are described herein, it will be appreciated that the invention is not limited to these specific methods of preparation.

The following examples will further illustrate the present invention but it will be understood that the invention is not limited to these examples.

EXAMPLES

Example 1. Difluoromethyl 2,2,3,3-tetrafluoropropyl ether (I).

The ether I was prepared and identified according to the procedure of Example 1 of U.S. Pat. No. 3,689,459, which is incorporated herein by reference.

Example 2. Difluoromethyl 2,2,3,3,3-pentafluoropropyl ether (II).

The ether II was prepared in a manner analogous to the preparation of the ether I of Example 1. Fractional distillation of the crude II gave II of 99.6% purity (by gas-liquid chromatography), $b_{760}$ 46.2°–46.3° C, $d_4^{22}$ 1.46, in 44% of theory based on the amount of 2,2,3,3,3-pentafluoropropanol employed. The structure of II was confirmed by proton NMR spectroscopy.

Example 3. Dichloromethyl 1,1,2,3,3,3-hexafluoropropyl ether (XXIV).

Methyl 1,1,2,3,3,3-hexafluoropropyl ether was stirred at 15°– 25° C. and irradiated with ultraviolet light as two molar equivalents of chlorine gas was added slowly. Analysis by GLC showed the product to be 76% XXIV, 15% $CCl_3$—O—$CF_2CHFCF_3$ and 8% $CH_2Cl$—O—$CF_2CHFCF_3$. Fractionational distillations of this product gave XXIV of 99.7% by GLC, $b_{760}$ 98.1°– 98.4° C. The structure of XXIV was confirmed by proton NMR spectroscopy.

Example 4. Difluoromethyl 1,1,2,3,3,3-hexafluoropropyl ether (III).

The ether XXIV of 97.9% purity (284 g, 1.13 moles) was stirred and kept between 0° – 10° C as bromine trifluoride (102 g, 0.746 mole) was added dropwise. Before the reaction was complete, it was stopped by the cautious addition of ice to decompose the remaining $BrF_3$. Then cold dilute sodium hydroxide solution was added to remove halogens and acids. The organic layer was separated, washed with water and dried; weight 219 g. Analyses by GLC and proton NMR showed this product to be 66% III and 31% CHFCl—O—$CF_2CHFCF_3$. Fractional distillation gave III of 99.9% purity, $b_{760}$ 47.0° – 47.3° C; $d_4^{23}$ 1.536; weight 113 g as well as CHFCl—O—$CF_2CHFCF_3$ of 97.6% purity, $b_{760}$ 69.9° – 70.3° C. Both structures were confirmed by proton NMR spectroscopy.

Example 5. Dichloromethyl 1,3-dichloro-1,1,2,3,3-pentafluoro-2-propyl ether (XXV).

1,3-Dichloro-1,1,2,3,3-pentafluoro-2-propyl methyl ether (303 g, 1.3 moles), $b_{760}$ 96.2° – 97.3° C, was chlorinated by addition of chlorine gas (193 g, 2.72 moles) at 15°– 25° C with the aid of ultraviolet irradiation. The product was freed of hydrogen chloride, dried and fractionally distilled at 45 torr to give XXV, $b_{45}$ 67.2° – 69.3° C, in 80% of the theoretical yield.

Example 6. Difluoromethyl 1,3-dichloro-1,1,2,3,3-pentafluoro-2-propyl ether (XXVI).

The ether XXV (296 g, 0.97 mole) and substantially anhydrous antimony trifluoride (185 g, 1.04 mole) were stirred at 60° C and antimony pentachloride (5.0 g, 0.017 mole) was added slowly. This mixture was heated to the reflux point at atmospheric pressure for two hours; then the product was distilled from the antimony halides at atmospheric pressure. The distillate was condensed, washed with acidified water then with neutral water, dried and fractionally distilled to give XXVI, $b_{760}$ 83.6° – 84.1° C, in 90% of the theoretical yield.

Example 7. Difluromethyl 1,1,2,3,3-pentafluoro-2-propyl ether (IV).

The ether XXVI (213 g, 0.79 mole) at 25° C was stirred as 0.9 M lithium aluminum hydride in diethylene glycol diethyl ether (484 ml, 0.436 mole of Li Al $H_4$) was added dropwise. Then the product was distilled at atmospheric pressure through a cold water condensor into an ice cooled receiver until 157 g of IV was collected. This distillate was fractionally distilled to give IV, $b_{760}$ 68.1° – 68.2° C, of 99.7% purity (by gas-liquid chromatography) in 93% of the theoretical yield; density at 23° C was 1.554. The structure of IV was confirmed by proton NMR spectroscopy.

Example 8. Chloromethyl 2,2,3,3,3-pentafluoropropyl ether (XXVII).

Methyl 2,2,3,3,3-pentafluoropropyl ether (225 g, 1.37 mole) in a flask fitted with a dry ice cooled condensor and moisture trap was stirred, heated to 33° C, irradiated with ultraviolet light, and sulfuryl chloride (174 g, 1.29 mole) was added dropwise. The reaction temperature dropped to about 0° C as $SO_2$ returned from the condensor. The condensor was allowed to warm gradually to permit $SO_2$ to escape and the reaction temperature to rise to about 33° C to complete the chlorination. The product was washed with ice cold water then with dilute sodium hydroxide solution to remove $SO_2$ and dried to give 250 g of crude XXVII. This was fractionally distilled to give XXVII, $b_{760}$ 87.1 – 88.5; yield 159 g, purity 92% by GLC. The structure of XXVII was confirmed by proton NMR spectroscopy.

Example 9. Fluoromethyl 2,2,3,3,3-pentafluoropropyl ether (V).

The ether XXVII was refractionated to obtain a sample (56.8 g, 0.286 mole) of > 99% purity by GLC. This sample was cooled to −5° C and stirred in a teflon bottle as bromine trifluoride (15.6 g, 0.114 mole) was added dropwise. The product was stirred with ice and dilute sodium hydroxide solution to remove halogens and acids, separated, washed with distilled water, freezedried at −20° C and then dried at 0° C over type 3A molecular sieve. The V so obtained was 99.0% by GLC; micro $b_{760}$ 62.2° C; $d_4^2$ 1.41; yield 45 g (87% of theory). The molecular sieve type 3A is manufactured and sold by the Linde Division of Union Carbide Company.

TABLE 1

CONVULSANT FLUOROMETHYL FLUOROPROPYL ETHERS

| COMPOUND | | $B_{760}$ C | MOUSE CONVULSANT CONC., VOL. % | MOUSE $LC_{50}$ VOL. % | ADDITIONAL REMARKS |
|---|---|---|---|---|---|
| I. | $CHF_2$—O—$CH_2CF_2CHF_2$[4] | 76 | 1.0 | 3.2 | CLONIC CONVULSIONS |
| II. | $CHF_2$—O—$CH_2CF_2CF_3$ | 46 | 1.4 | > 4.2 | CLONIC AND TONIC CONVULSIONS, CATALEPSY |
| III. | $CHF_2$—O—$CH_2CHFCF_3$ | 47 | 2.0 | > 12 | |
| IV. | $CHF_2$—O—$CF(CHF_2)_2$[2] | 68 | 1.2 | 5.3 | CONVULSIONS AND SEDATION |

TABLE 1-continued

CONVULSANT FLUOROMETHYL FLUOROPROPYL ETHERS

|  | COMPOUND | $B_{760}$ C | MOUSE CONVULSANT CONC., VOL. % | MOUSE $LC_{50}$ VOL. % | ADDITIONAL REMARKS |
|---|---|---|---|---|---|
| V. | $CH_2F-O-CH_2CF_2CF_3$[1] | 62 | 1.5 | > 3.0 | OPISTHOTONOID CONV. IN DOGS METRAZOLE-LIKE CONVULSIONS |
| VI. | $CF_3-O-CH_2CF_2CHF_2$[3] | 45.5 | ≤ 0.5 | ≤ 0.5 | "VIOLENT CONVULSIONS AND DEATH IN 30–120 SEC."[3] |
| VII. | $CF_3-CH_2-O-CH_2CF_3$ | 64 | ≤ 0.25[5] | < 0.50[5] | CLONIC AND TONIC CONVULSIONS IN 30 SEC. |

[1]WEINMAYR, U.S. Pat. No. 2,992,276.
[2]REGAN AND ZIMMERMAN, FED. PROC. ABS., 30(2), 442 (1971).
[3]ALDRICH AND SHEPPARD, J. ORG. CHEM. 29, 11–15 (1954).
[4]REGAN, U.S. Pat. No. 3,689,459.
[5]KRANTZ, RUDO AND LOECHER, PROC. SOC. EXP. BIOL. MED., 124, 820–2 (1967).

TABLE 2

NONCONVULSANT FLUOROMETHYL FLUOROPROPYL ETHERS

|  | COMPOUND | $B_{760}$ C | MOUSE $AC_{50}$ VOL. % | MOUSE $LC_{50}$ VOL. % | ADDITIONAL REMARKS |
|---|---|---|---|---|---|
| VII. | $CHF_2-O-CHFCF_2CHF_2$[4] | 75 | 0.61 | 6.5 | NONCONVULSANT IN DOGS |
| IX. | $CHF_2-O-CHFCF_2CF_3$ | 44.5 | 4.3 | > 9.9 |  |
| X. | $CHF_2-O-CH(CF_3)_2$[2,7] | 42 | 2.5 | 12 | NONCONVULSANT IN DOGS |
| XI. | $CHF_2-O-CH(CF_3)CHF_2$[2] | 65.5 | 0.84 | 4.9 |  |
| XII. | $CHF_2-O-CH(CHF_2)_2$[2] | 90 | 0.64 | 3.8 |  |
| XIII. | $CH_2F-O-CF_2CHFCF_3$ | 69 | 2.1 | 6.4 |  |
| XIV. | $CH_2F-O-CF(CF_3)CHF_2$[2] | 64 | 2.5 | 9.0 | NONCONVULSANT IN DOGS |
| XV. | $CH_2F-O-CH(CF_3)_2$[2,6] | 58.5 | 1.4 | 8.5 | NONCONVULSANT IN DOGS |
| XVI. | $CH_2F-O-CH(CF_3)CHF_2$[2] | 78.5 | 0.84 | 5.1 |  |

[6]REGAN AND LONGSTREET, U.S. Pat. No. 3,683,592.
[7]CROIX AND SZUR, U.S. Pat. No. 3,476,860.

TABLE 3

NONCONVULSANT METHYL FLUOROPROPYL ETHERS

|  | COMPOUND | $B_{760}$ C | MOUSE $AC_{50}$ VOL. % | MOUSE $LC_{50}$ VOL. % | ADDITIONAL REMARKS |
|---|---|---|---|---|---|
| XVII. | $CH_3-O-CF_2CF_2CF_3$ | 34 | n.a.[15] | 50 | DEATH DUE TO ANOXIA |
| XVIII. | $CH_3-O-CF_2CHFCF_3$[9,12] | 54 | 3.9 | > 8.0 |  |
| XIX. | $CH_3-O-CH_2CF_2CF_3$[11] | 47.5 | 11 | 16 | "EXTENSOR RIGIDITY OF HIND LEGS AND TREMORS IN DOGS"[11] |
| XX. | $CH_3-O-CH_2CF_2CHF_2$ | 73 | 2.5 | 7.0 |  |
| XXI. | $CH_3-O-CH(CF_3)_2$[2,5,13] | 51 | 2.2 | 9.0 | NONCONVULSANT IN DOGS; ANTAGONIST TO FLUROTHYL[5] |
| XXII. | $CH_3-O-CH(CF_3)CHF_2$[2] | 61 | 1.5 | 6.9 |  |
| XXIII. | $CH_3-O-CH(CHF_2)_2$[2,10] | 82 | 1.4 | > 7.8 |  |

[8]WARNELL, U.S. Pat. No. 3,449,389.
[9]RENDALL AND PEARLSON, U.S. Pat. No. 2,730,543.
[10]GILBERT AND VELDHUIS, U.S. Pat. No. 3,445,524.
[11]LU, LING AND KRANTZ, ANESTHESIOLOGY, 14, 466 (1953).
[12]DEAR AND GILBERT, U.S. Appl. (P.D. File 5300–1238), 12 OCTOBER 1967, Ser. No. 674,746, NOW U.S. Pat. No. 3,557,294.
[13]GILBERT AND VELDHUIS, U.S. Pat. No. 3,346,448.
[14]ROBBINS, J. PHARMACOLOGY AND EXPERIMENTAL THERAPEUTICS, 86, 197–204 (1946).
[15]NON-ANESTHETIC Various other examples and modifications of the foregoing examples will be apparent to those skilled in the art after reading the foregoing specification and the appended claims without departing from the spirit and scope of the invention. All such further examples and modifications are included within the scope of the invention as defined in the following claims.

What is claimed is:

1. The method of convulsive therapy comprising inducing a therapeutic convusion in an animal by administering to said animal an effective amount for inducing a therapeutic convulsion of the compound $CHF_2-O-CH_2CF_2CHF_2$ in vapor form by inhalation while maintaining respiration of said animal.

* * * * *